United States Patent
Hsieh et al.

(10) Patent No.: US 12,268,756 B2
(45) Date of Patent: Apr. 8, 2025

(54) BIOCOMPATIBLE MAGNETIC MATERIALS

(71) Applicant: MegaPro Biomedical Co., Ltd., Zhubei (TW)

(72) Inventors: Wen-Yuan Hsieh, Hsinchu (TW); Yuan-Hung Hsu, Hsinchu (TW); Chia-Wen Huang, Hsinchu (TW); Ming-Cheng Wei, Taoyuan (TW); Chih-Lung Chen, Taichung (TW); Shian-Jy Wang, Hsinchu (TW)

(73) Assignee: MegaPro Biomedical Co. Ltd., Hsinchu (TW)

( * ) Notice: Subject to any disclaimer, the term of this patent is extended or adjusted under 35 U.S.C. 154(b) by 0 days.

(21) Appl. No.: 17/535,168

(22) Filed: Nov. 24, 2021

(65) Prior Publication Data

US 2022/0080057 A1 Mar. 17, 2022

Related U.S. Application Data

(63) Continuation of application No. 16/204,510, filed on Nov. 29, 2018, now abandoned.

(30) Foreign Application Priority Data

Feb. 12, 2018 (CN) .......................... 201810145800.0

(51) Int. Cl.
| | | |
|---|---|---|
| A61K 49/08 | (2006.01) | |
| A61K 49/12 | (2006.01) | |
| A61K 49/18 | (2006.01) | |

(52) U.S. Cl.
CPC .......... *A61K 49/085* (2013.01); *A61K 49/126* (2013.01); *A61K 49/1824* (2013.01); *A61K 49/1839* (2013.01); *A61K 49/186* (2013.01); *A61K 49/1875* (2013.01)

(58) Field of Classification Search
CPC .................. A61K 49/12; A61K 49/186; A61K 49/1824; A61K 49/126; C08G 83/001
See application file for complete search history.

(56) References Cited

U.S. PATENT DOCUMENTS

| 2009/0041674 A1 | 2/2009 | Jones et al. |
| 2011/0059025 A1 | 3/2011 | Pritchard et al. |
| 2012/0269896 A1 | 10/2012 | Hakata et al. |

FOREIGN PATENT DOCUMENTS

| CN | 102112158 A | 6/2011 |
| CN | 102552945 A | 7/2012 |
| CN | 103405789 A | 11/2013 |
| CN | 107073035 A | 8/2017 |
| CN | 107073140 A | 8/2017 |
| EP | 2965754 A1 | 1/2016 |
| EP | 2974745 A1 | 1/2016 |
| JP | 2006028032 | 2/2006 |
| JP | 2007277131 | 10/2007 |
| JP | 2009531302 | 9/2009 |
| JP | 2011126876 | 6/2011 |
| JP | 2011519843 | 7/2011 |
| WO | WO-2009/129649 A1 | 10/2009 |
| WO | WO2016073313 A1 | 5/2016 |

OTHER PUBLICATIONS

He et al. "Availability and toxicity of Fe(II) and Fe(III) in Caco-2 cells", J. Zhejiang Univ. Sci. B 9, 707-712 (2008) (Year: 2008).*
Basti et al "Catechol Derivatives-Coated $Fe_3O_4$ and $\gamma$-$Fe_2O_3$ Nanoparticles as Potential MRI Contrast Agents" Journal of Colloid and Interface Science vol. 341, pp. 248-254, 2010.
Li et al "Superparamagnetic Iron Oxide Nanoparticles as MRI Contrast Agents for Non-Invasive Stem Cell Labeling and Tracking" Theranostics vol. 3, pp. 595-615, 2013.
Wu et al "Reactive Oxygen Species-Related Activities of Nano-Iron Metal and Nano-Iron Oxides" Journal of Food and Drug Analysis vol. 22, pp. 86-44, 2014.
Laurent et al. "Magnetic Iron Oxide Nanoparticles: Synthesis, Stabilization, Vectorization, Physicochemical Characterizations, and Biological Applications", Chem. Rev. 2008, 108, 2064-2110 (Year: 2008).

* cited by examiner

*Primary Examiner* — James W Rogers
(74) *Attorney, Agent, or Firm* — Morse, Barnes-Brown & Pendleton, P.C.; Russell L. Widom

(57) ABSTRACT

A biocompatible magnetic material containing an iron oxide nanoparticle and one or more biocompatible polymers, each having formula (I) below, covalently bonded to the iron oxide nanoparticle:

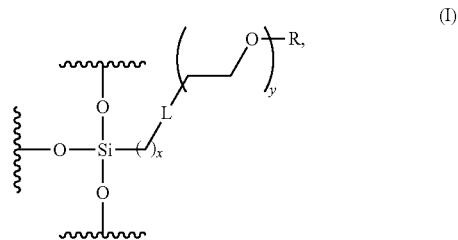

in which each of variables R, L, x, and y is defined herein, the biocompatible magnetic material contains 4-15% Fe(II) ions relative to the total iron ions. Also disclosed in a method of preparing the biocompatible magnetic material.

16 Claims, 2 Drawing Sheets

BIOCOMPATIBLE MAGNETIC MATERIALS

CROSS-REFERENCE TO RELATED APPLICATIONS

The present application is a continuation of U.S. patent application Ser. No. 16/204,510, filed on Nov. 29, 2018, which claims the priority of Chinese Invention Patent Application No. 201810145800.0, filed on Feb. 12, 2018. The content of the two prior applications is hereby incorporated by reference in its entirety.

BACKGROUND

Iron oxide nanoparticles are useful as contrast agents for magnetic resonance imaging (MRI) because of their chemical stability and suitable magnetization. Magnetite ($Fe_3O_4$) and maghemite ($\gamma$-$Fe_2O_3$) are two examples of superparamagnetic iron oxide nanoparticles.

These iron oxide nanoparticles are capable of conjugating with biocompatible polymers to form biocompatible magnetic materials, e.g., MRI contrast agents.

Conventionally, $Fe_3O_4$ magnetic nanoparticles are synthesized by using a mixture of Fe(II) and Fe(III) salts. In theory, $Fe_3O_4$ magnetic nanoparticles contain about 33% Fe(II) ions relative to the total iron ions. Differently, $\gamma$-$Fe_2O_3$ magnetic nanoparticles contain 0% Fe(II) ions.

$Fe_3O_4$ provides stronger $T_2$ shortening effect, i.e., higher relaxivity r2, than $\gamma$-$Fe_2O_3$. See, e.g., Basti et al., J Colloid Interface Sci., 2010, 341: 248-254; and Li et al., Theranostics, 2013, 3(8): 595-615. On the other hand, $Fe_3O_4$ nanoparticles are significantly more effective in producing hydroxyl radicals than $\gamma$-$Fe_2O_3$ nanoparticles and, as a result, $Fe_3O_4$ may induce higher toxicity compared to $\gamma$-$Fe_2O_3$ in clinical applications. See, e.g., Park et al., Arch Toxicol., 2014, 88(8): 1607-1618; and Wu et al., Journal of Food and Drug Analysis, 2014, 22, 86-94.

There is a need to develop a new biocompatible magnetic material that has high relaxivity and low toxicity.

SUMMARY

The present invention relates to certain biocompatible magnetic materials that can be used as MRI contrast agents with high relaxivity and low toxicity.

In one aspect of this invention, it covers biocompatible magnetic materials that contain an iron oxide nanoparticle and one or more biocompatible polymers, each having formula (I) below, covalently bonded to the iron oxide nanoparticle:

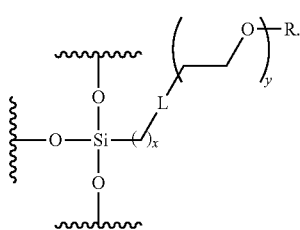

(I)

In this formula, R is H, $C_1$-$C_6$ alkyl, $C_2$-$C_6$ alkenyl, $C_2$-$C_6$ alkynyl, $C_3$-$C_{10}$ cycloalkyl, $C_1$-$C_{10}$ heterocycloalkyl, aryl, heteroaryl, a $C_1$-$C_{10}$ carbonyl group, or a $C_1$-$C_{10}$ amine group; L is a linker; x is 1 to 10; and y is 5 to 1000.

Notably, the biocompatible magnetic materials each contain 4-15% Fe(II) ions relative to the total iron ions.

The iron oxide nanoparticle can have a Fe(II) content the same as or different from that contained in a biocompatible magnetic material. An exemplary iron oxide nanoparticle contains 4-15% (e.g., 4-10% and 4-8%) Fe(II) ions relative to the total iron ions in it.

Referring to formula (I) above, the linker F can be O, S, Si, $C_1$-$C_6$ alkylene, a carbonyl moiety containing two carbonyl groups and 2-20 carbon atoms, or a group having one of the following formulas:

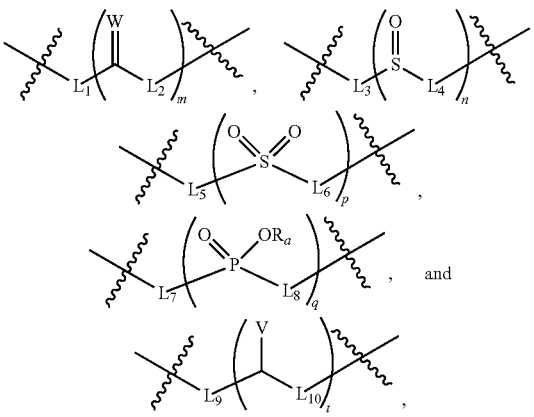

in which each of m, n, p, q, and t, independently, is 1-6; W is O, S, or $NR_b$; each of $L_1$, $L_3$, $L_5$, $L_7$, and $L_9$, independently, is a bond, O, S, or $NR_c$; each of $L_2$, $L_4$, $L_6$, $L_8$, and $L_{10}$, independently, is a bond, O, S, or $NR_d$; and V is $OR_e$, $SR_f$, or $NR_gR_h$, each of $R_a$, $R_b$, $R_c$, $R_d$, $R_e$, $R_f$, $R_g$, and $R_h$, independently, being H, OH, a $C_1$-$C_{10}$ alkyl, a $C_1$-$C_{10}$ heteroalkyl, a $C_3$-$C_{10}$ cycloalkyl, a $C_1$-$C_{10}$ heterocycloalkyl, aryl, or heteroaryl.

The term "alkyl" herein refers to a saturated, linear or branched hydrocarbon moiety, such as methyl, ethyl, propyl, butyl, pentyl, and hexyl. The term "alkenyl" refers to a linear or branched hydrocarbon moiety that contains at least one double bond, such as —CH=CH—CH$_3$ and —CH=CH—CH$_2$—. The term "alkynyl" refers to a linear or branched hydrocarbon moiety that contains at least one triple bond, such as —C≡C—CH$_3$ and —C≡C—CH$_2$—. The term "cycloalkyl" refers to a saturated, cyclic hydrocarbon moiety, such as cyclohexyl and cyclohexylene. The term "heterocycloalkyl" refers to a saturated, cyclic hydrocarbon moiety containing at least one heteroatom selected from N, O, P, B, S, Si, Sb, Al, Sn, As, Se, and Ge, such as piperazinyl and piperidinyl.

The term "heteroalkyl" herein refers to an aliphatic moiety containing at least one heteroatom selected from N, O, P, B, S, Si, Sb, Al, Sn, As, Se, and Ge. Examples of heteroalkyl include methoxymethyl and methylaminoethyl.

The term "aryl" herein refers to a $C_6$ monocyclic, $C_{10}$ bicyclic, $C_{14}$ tricyclic, $C_{20}$ tetracyclic, or $C_{24}$ pentacyclic aromatic ring system. Examples of aryl groups include phenyl, phenylene, naphthyl, naphthylene, anthracenyl, anthracenylene, pyrenyl, and pyrenylene. The term "heteroaryl" herein refers to an aromatic 5-8 membered monocyclic, 8-12 membered bicyclic, 11-14 membered tricyclic, and 15-20 membered tetracyclic ring system having one or more heteroatoms (such as O, N, S, or Se).

Examples of heteroaryl groups include furyl, furylene, fluorenyl, fluorenylene, pyrrolyl, pyrrolylene, thienyl, thienylene, oxazolyl, oxazolylene, imidazolyl, imidazolylene, benzimidazolyl, benzimidazolylene, thiazolyl, thiazolylene, pyridyl, pyridylene, pyrimidinyl, pyrimidinylene, quinazolinyl, quinazolinylene, quinolinyl, quinolinylene, isoquinolyl, isoquinolylene, indolyl, and indolylene.

Unless specified otherwise, alkyl, alkenyl, alkynyl, cycloalkyl, heterocycloalkyl, heteroalkyl, aryl, and heteroaryl mentioned herein include both substituted and unsubstituted moieties. Possible substituents on cycloalkyl, cycloalkylene, cycloalkenyl, cycloalkenylene, cycloalkynyl, cycloalkynylene, heterocycloalkyl, heterocycloalkylene, heterocycloalkenyl, heterocycloalkenylene, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_2$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on aliphatic, heteroaliphatic, oxyaliphatic, alkyl, alkylene, alkenyl, alkenylene, alkynyl, and alkynylene include all of the above-recited substituents except $C_1$-$C_{10}$ alkyl. Cycloalkyl, cycloalkylene, cycloalkenyl, cycloalkenylene, heterocycloalkyl, heterocycloalkylene, heterocycloalkenyl, heterocycloalkenylene, aryl, and heteroaryl can also be fused with each other.

Further covered by this invention is a method for preparing a biocompatible magnetic material described above.

The method includes four steps: (i) providing a first solution that contains an iron oxide nanoparticle in a first organic solvent, the iron oxide nanoparticle containing 4-15% Fe(II) ions relative to the total iron ions; (ii) providing a second solution that contains a biocompatible polymer of formula (I) in a second organic solvent; (iii) mixing the first solution and the second solution to afford a mixed solution; and (iv) adding water to the mixed solution and stirring the resulting solution for at least 20 hours to obtain a biocompatible magnetic material.

Preferably, the iron oxide nanoparticle is formed by mixing a hydroxide solution with an iron solution that contains a Fe(II) salt under an inert gas atmosphere.

The details of one or more embodiments are set forth in the description below. Other features, objects, and advantages of the embodiments will be apparent from the description and the claims.

BRIEF DESCRIPTION OF THE DRAWINGS

The description below refers to the accompanying drawings, of which.

DETAILED DESCRIPTION

Figure 1:
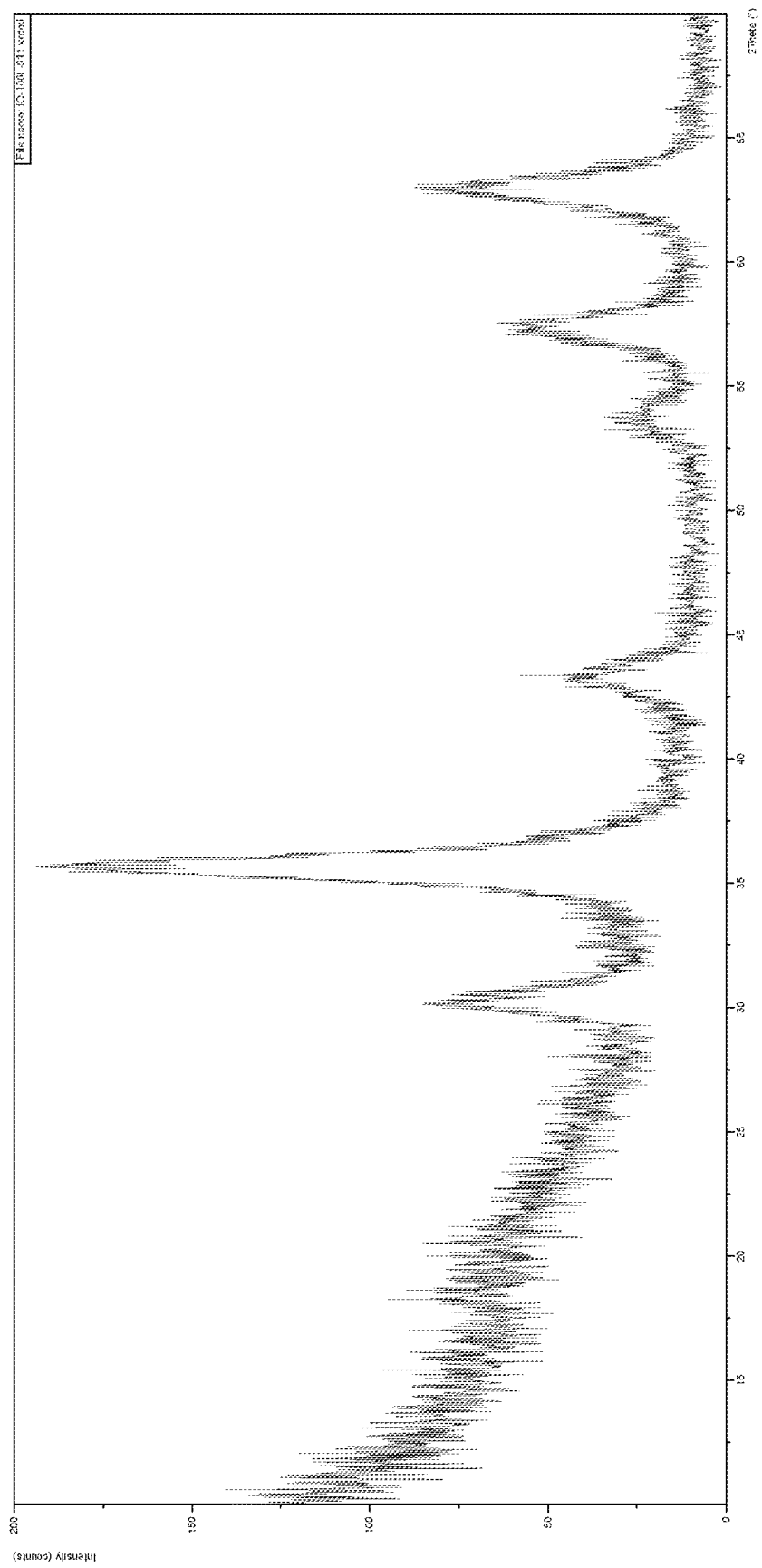
FIG. 1 is an X-ray powder diffraction ("XRPD") pattern for iron oxide-oleic acid nanoparticles ("IO-OA") batch 4.

Disclosed in detail herein is a biocompatible magnetic material that contains an iron oxide nanoparticle and one or more biocompatible polymers covalently bonded to the iron oxide nanoparticle.

The iron oxide nanoparticle can be a superparamagnetic core having a particle size of 1 to 100 nm (e.g., 2 to 50 nm and 5 to 25 nm). Preparation of a superparamagnetic core is well known in the art. See Laurent et al., Chem. Rev., 2008, 108, 2064-2110.

The iron oxide nanoparticle is typically formed of an organic acid or a salt thereof. Examples of the organic acid or salt include, but are not limited to, oleic acid and a salt thereof.

Of note, the iron oxide nanoparticle preferably contains 4-15% Fe(II) ions relative to the total iron ions in it. An exemplary iron oxide nanoparticle contains 4-10% or 4-8% Fe(II) ions relative to the total iron ions. The content of Fe(II) ions in an iron oxide nanoparticle is important for a biocompatible magnetic material to exert high relaxivity and low toxicity. More specifically, a low Fe(II) content, e.g., less than 4% Fe(II) ions relative to the total iron ions, typically exhibits low relaxivity. On the other hand, a high Fe(II) content, e.g., greater than 15% Fe(II) ions relative to the total iron ions, can cause high toxicity.

The biocompatible magnetic material also contains one or more biocompatible polymers to enhance its biocompatibility. Each of the biocompatible polymers has formula (I) below:

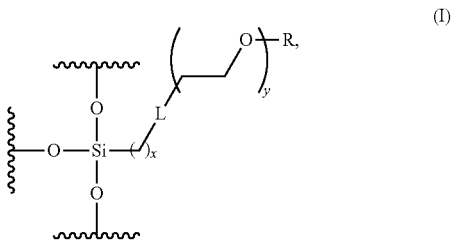

(I)

in which variables R, L, x, and y are defined in the SUMMARY section.

In one embodiment, the iron oxide nanoparticle is covalently bonded to one or more biocompatible polymers each having the following formula:

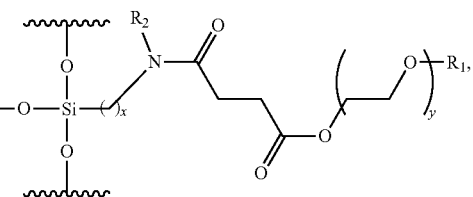

in which $R_1$ is H, $C_1$-$C_6$ alkyl, $C_2$-$C_6$ alkenyl, $C_2$-$C_6$ alkynyl, $C_3$-$C_{10}$ cycloalkyl, $C_1$-$C_{10}$ heterocycloalkyl, aryl, heteroaryl, a $C_1$-$C_{10}$ carbonyl group, or a $C_1$-$C_{10}$ amine group; $R_2$ is H, $C_1$-$C_6$ alkyl, $C_2$-$C_6$ alkenyl, $C_2$-$C_6$ alkynyl, $C_3$-$C_{10}$ cycloalkyl, $C_1$-$C_{10}$ heterocycloalkyl, aryl, or heteroaryl; x is 1 to 10; and y is 5 to 1000.

Preferably, $R_1$ is $C_1$-$C_6$ alkyl, a $C_1$-$C_{10}$ carbonyl group, or a $C_1$-$C_{10}$ amine group, and $R_2$ is H or $C_1$-$C_6$ alkyl. For example, $R_1$ is methyl (—$CH_3$), carboxyl (—COOH), or amino (—$NH_2$), and $R_2$ is H.

When $R_1$ is carboxyl (—COOH) or amino (—$NH_2$), the carboxyl-terminated or amine-terminated biocompatible polymer can be coupled with a biological molecule, e.g., folic acid. For example, the folic acid allows coupling with an amine-terminated biocompatible polymer by forming a —CONH— linkage.

The biocompatible magnetic material of this invention can be coupled to a specific targeting agent for biological applications. Examples of a specific targeting agent include, but art not limited to, an antibody, a protein, a peptide, an enzyme, a carbohydrate, a glycoprotein, a nucleotide, and a lipid. In an exemplary biocompatible magnetic material, $R_1$ is coupled to an antibody (e.g., My10).

Still within the scope of this invention is a method for preparing the above-described biocompatible magnetic material.

Again, the method includes the following steps: providing a first solution that contains an iron oxide nanoparticle in a first organic solvent, in which the iron oxide nanoparticle contains 4-15% Fe(II) ions relative to the total iron ions; providing a second solution that contains biocompatible polymers of formula (I) in a second organic solvent; mixing the first solution and the second solution to afford a mixed solution; and adding water to the mixed solution and stirring the resulting solution for at least 20 hours to obtain a biocompatible magnetic material.

The iron oxide nanoparticle used in the method is typically formed by mixing a hydroxide solution with an iron solution that contains a Fe(II) salt under an inert gas atmosphere.

An exemplary iron solution contains a Fe(II) salt (e.g., $FeCl_2$) and a Fe(III) salt (e.g., $FeCl_3$), in which the mole ratio of Fe(III)/Fe(II) is 1.70 or higher (e.g., 1.75 or higher, 1.80 or higher, and 1.90 or higher).

The hydroxide solution can be a sodium hydroxide solution having a concentration of 2 N or lower (e.g., 1.5 N or lower and 1 N or lower).

Examples of the inert gas include, but are not limited to, nitrogen and argon.

To reiterate, the iron oxide nanoparticle can be formed of an organic acid or a salt thereof. An exemplary organic acid or salt is oleic acid or a salt thereof. When oleic acid is used, it can be present in an amount of 100 mF or less (e.g., 90 mF or less, 70 mF or less, and 50 mF or less) per mole iron.

In one example, the iron oxide nanoparticle is formed from oleic acid and an iron solution containing $FeCl_2$ and $FeCl_3$, affording an iron oxide-oleic acid nanoparticle or IO-OA. This exemplary iron oxide nanoparticle can be prepared as follows: mixing $FeCl_2$ and $FeCl_3$ in a solvent (e.g., water), adding a sodium hydroxide solution (e.g., 1 N) under nitrogen to the above mixture, and treating the solution thus obtained with oleic acid to form an IO-OA nanoparticle.

The iron oxide nanoparticle is preferably collected, after the treatment with an organic acid or a salt thereof, by removing water, dissolving it in toluene, and centrifuging the liquid thus obtained to eliminate certain large particles.

Turning to the biocompatible polymers used in the method, they include the polymers themselves, as well as their salts and solvates, if applicable. A salt, for example, can be formed between an anion and a positively charged group (e.g., amino) on a polymer. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a polymer. Suitable cations include sodium ion, potassium ion, magnesium ion, calcium ion, and an ammonium cation such as tetramethylammonium ion. The polymers also include those salts containing quaternary nitrogen atoms. A solvate refers to a complex formed between a polymer and a pharmaceutically acceptable solvent. Examples of a pharmaceutically acceptable solvent include water, ethanol, isopropanol, ethyl acetate, acetic acid, and ethanolamine.

Scheme (I) below shows a process of preparing an exemplary silane-containing biocompatible polymer.

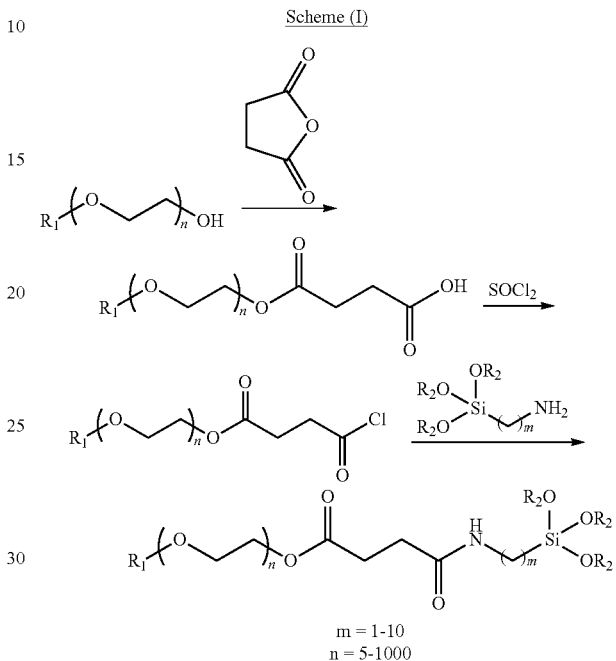

As shown in the scheme above, alkoxyl-polyethylene glycol (molecular weight 2000) reacts with succinic anhydride in the presence of a base (e.g., dimethylaminopyridine) to form mPEG-COOH, which is subsequently converted to mPEG-COCl using thionyl chloride. Mixing mPEG-COCl with (3-aminopropyl)-triethoxysilane yields mPEG-silane.

A skilled person in the art can modify the process shown in Scheme (I) to prepare biocompatible polymers using well-known methods. See R. Larock, Comprehensive Organic Transformations (VCH Publishers 1989); T. W. Greene and P. G. M. Wuts, Protective Groups in Organic Synthesis ($3^{rd}$ Ed., John Wiley and Sons 1999); L. Fieser and M. Fieser, Fieser and Fieser's Reagents for Organic Synthesis (John Wiley and Sons 1994); and L. Paquette, ed., Encyclopedia of Reagents for Organic Synthesis (John Wiley and Sons 1995) and subsequent editions thereof. Specific routes that can be used to synthesize the biocompatible polymers can be found in: (a) Rist et al., Molecules 2005, 10, 1169-1178, (b) Koheler et al., JACS, 2004, 126, 7206-7211; and (c) Zhang et al., Biom mircod 2004, 6:1 33-40.

To perform the method for preparing a biocompatible magnetic material, a first solution containing the above-described iron oxide nanoparticle is formed in a first organic solvent, and a second solution containing the above-described biocompatible polymers is provided in a second organic solvent.

Each of the first organic solvent and the second organic solvent, independently, can be toluene, aliphatic hydrocarbon, tetrahydrofuran, ketone, alcohol, alkyl ester, or a combination thereof. Preferably, both organic solvents are toluene.

Upon mixing the first solution and the second solution to afford a mixed solution, it is important to perform the step of adding water as a catalyst to the mixed solution and stirring the resulting solution for at least 20 hours to afford a biocompatible magnetic material.

As described above, the iron oxide nanoparticle used in the method contains 4-15% Fe(II) ions relative to the total iron ions in it. After performing the method, a biocompatible magnetic material thus obtained typically contains 4-15% Fe(II) ions relative to the total iron ions.

The biocompatible polymer synthesized in Scheme (I) above is useful in that it can chemically modify the surface of the iron oxide nanoparticle to increase biocompatibility. In addition, the biocompatible polymer is useful in that it can label particles (e.g., nanoparticles, magnetic particles, magnetic nanoparticles, and superparamagnetic particles), to render the particles to be further reactive toward one or more targeting, fluorescent, therapeutic, or diagnostic agents.

The targeting agent is preferably coupled to the biocompatible polymer via covalent bonds. Commonly used targeting agents include an antibody, a protein, a peptide, an enzyme, a carbohydrate, a glycoprotein, a nucleotide, and a lipid. The biocompatible magnetic material may have a diameter of about 3-500 nm after coupling with the targeting agent. Those skilled in the art can attach any suitable targeting agents on the nanoparticle to give specificity thereto. For example, folic acid can be used to specify breast cancer cells with a folate receptor. The structure of the folic acid allows coupling with an amine-terminated or carboxy-terminated biocompatible polymer. For example, the folic acid allows coupling with the amine-terminated biocompatible polymer by forming a —CONH— linkage.

Without further elaboration, it is believed that one skilled in the art can, based on the description herein, utilize the present embodiments to their fullest extent. The following specific examples below are to be construed as merely illustrative, and not limitative of the remainder of the disclosure in any way whatsoever. All publications cited herein are incorporated by reference in their entirety.

Example 1: Preparation of Biocompatible Magnetic Materials

Two biocompatible magnetic materials were prepared following the procedures described below.
Preparation of Iron Oxide-Oleic Acid (IO-OA) Nanoparticles A mixture of $FeCl_2.4H_2O$ (900 g; 4.53 mole), $FeCl_3$ (1327 g; 8.18 mole), and water (23.6 L) was stirred at 150-200 rpm in a 100 L glass reactor at 25° C. A sodium hydroxide solution (1N) was added under nitrogen to the reactor at a rate of 0.2-0.3 kg/min, resulting in a pH value of 11-12. Subsequently, oleic acid (800 mL; 63 mL per mole iron) was added and the resulting mixture was stirred for additional 60 minutes, thereby forming IO-OA nanoparticles as a dark paste in an aqueous solution. The water was removed after the pH of the water solution was adjusted to a pH value of 1 to 2 with hydrochloric acid (3 N). 12 L toluene was then added to the remaining dark paste to suspend crude IO-OA nanoparticles in the toluene solution. The crude IO-OA nanoparticles in toluene were centrifuged at 6000 rpm for 15 minutes to obtain IO-OA nanoparticles in toluene.
Preparation of Biocompatible Polymers mPEG-silane-750 and mPEG-silane-2000

A biocompatible polymer mPEG-silane-750 was prepared as follows. A mixture of 300 g (0.4 moles) of methoxy-PEG (mPEG, molecular weight 750), succinic anhydride (48 g; 0.48 moles) and 4-dimethylamino-pyridine (DMAP; 19.5 g; 0.159 moles) were allowed to sit in a 1000-mL round bottom flask under vacuum (20 Torrs) for 2 hours. 600 mL of toluene was added to the mixture, which was then stirred at 30° C. for one day to form mPEG-COOH. Subsequently, 36 mL (0.48 moles) of thionyl chloride was added at a rate of 1 mL/min and the mixture was stirred for 2-3 hours. Thereafter, 333.8 mL (2.4 moles) of triethylamine was added at a rate of 1 mL/min to obtain pH around 6-7. After cooling to room temperature, the mixture containing mPEG-COCl was reacted with 94.5 mL (0.4 moles) of 3-aminopropyl triethoxy silane at room temperature for at least 8 hours to yield crude mPEG-silane-750. The crude mPEG-silane-750 was precipitated after 9 L of isopropyl ether was added to the reaction mixture. A solid product was collected by filtration, re-dissolved in 500 mL of toluene, and centrifuged at 5000 rpm for 5 minutes to collect a supernatant, to which was added 9 L of isopropyl ether. A brown oily liquid was separated from the isopropyl ether and dried under vacuum to obtain the biocompatible polymer mPEG-silane-750.

A biocompatible polymer mPEG-silane-2000 was prepared as follows. Methoxy-PEG (mPEG, molecular weight 2000) (3 kg) was added to a 20 L reaction vessel, equipped with a Dean-Stark Trap. 15 L toluene was added to the reaction vessel and the reaction mixture was stirred at 150±20 rpm with a mechanical stirrer. The reaction was conducted at 120° C. and refluxed for 60 minute. Succinic anhydride (SA, 180 g) and 4-Dimethylaminopyridine (DMAP, 70 g) were then added to the reaction vessel and the reaction was continued for 20 hours at 65° C. to form mPEG-COOH. Subsequently, 170 g of thionyl chloride ($SOCl_2$) was added to the reaction vessel, with $N_2$ gas blanket over reaction and reaction continued for 3 hours. Thereafter, triethylamine (TEA, 436 g) was added to the reaction vessel and stirred at 250 rpm. After cooling to room temperature, the mixture containing mPEG-COCl was reacted with 300 g of 3-aminopropyl triethoxysilane at room temperature for at least 8 hours to yield crude mPEG-silane-2000. The crude material thus obtained was then filtered to remove salts and give a clear brown solution as mPEG-silane-2000.
Preparation of Biocompatible Polymers COOH-PEG-silane-750 and COOH-PEG-silane-2000

300 g (0.4 mole) of PEG (molecular weight: 750) and 600 mL of N-methyl-2-pyrrolidone were placed in a 1000 mL round bottom flask and heated to 60° C. under vacuum (20 Torr) for more than 2 hours. 88 g (0.88 mole) of succinic anhydride and 19.5 g (0.16 mole) of 4-dimethylamino-pyridine (DMAP) were added for reaction at 30° C. for two days, thus obtaining dicarboxy-terminated PEG (COOH-PEG).

36 ml (0.48 mole) of thionyl chloride was added at a rate of 1 mL/min and stirred for 2-3 hours. Subsequently, 133.8 mL (0.96 mole) of triethylamine was added at a rate of 1 mL/min. 94.5 mL (0.4 mole) of 3-aminopropyl triethoxysilane was then added to the reaction for at least 12 hours. The reaction mixture was added to 9 L of cold isopropyl ether for re-precipitation, and the resulting precipitates were collected, re-dissolved in 100 mL of dichloromethane. The mixture thus obtained was again added to 9 L of cold isopropyl ether for re-precipitation. An off-white precipitate was collected and dried under vacuum for 2 days, thus obtaining a biocompatible polymer, i.e., COOH-PEG-silane-750.

A biocompatible polymer COOH-mPEG-silane-2000 was prepared following the same procedure described above using a mixture of 800 g (0.4 moles) of PEG (PEG, molecular weight 2000), succinic anhydride (88 g; 0.88 moles), and 4-dimethylamino-pyridine (DMAP; 19.5 g; 0.16 moles).

Preparation of a Biocompatible Magnetic Material with mPEG-silane-2000

A biocompatible magnetic material was prepared by conjugating mPEG-silane-2000 with an iron oxide nanoparticle, i.e., IO-OA nanoparticle, in toluene as follows.

A toluene solution of IO-OA nanoparticle (6 mg Fe/mL, 700 mL) and a toluene solution of mPEG-silane-2000 (160 mg/mL, 500 mL) were mixed in a 2 L round bottom flask with water being added to the resulting solution. After 24 hours reaction, mPEG-silane-2000 conjugated iron oxide nanoparticles were extracted by water, and filtration to remove large particles to afford an clear aqueous solution. The resulting aqueous solution was purified and concentrated with an ultra-filtration device to obtain a biocompatible magnetic material labeled as IO-OA/mPEG-silane-2000.

Preparation of a Biocompatible Magnetic Material with COOH-PEG-silane-2000

250 g of COOH-mPEG-silane-2000 was added to 1-1.2 L of a toluene solution containing 10 g Fe of IO-OA nanoparticle. The resulting mixture was sonicated for 2-3 hours. After addition of 1.5 L of deionized water, the mixture was purified by an ultra-filtration device and concentrated to 100 mL to obtain a biocompatible magnetic material labeled as IO-OA/COOH-PEG-silane-2000.

Example 2: Characterization of Iron Oxide Nanoparticles and Biocompatible Magnetic Materials A study was performed to characterize a biocompatible magnetic material prepared in EXAMPLE 1, as well as certain iron oxide nanoparticles, as follows.

Fe(II) Ion Determination

Fe(II)/Fe(III) ion ratios of iron oxide nanoparticles and biocompatible magnetic materials were measured by Iron Test kit (Spectroquant 1.00796.0001, Merck). The reagent in the test kit, i.e., 1,10-plenanthroline, was sensitive for Fe(II) ion but not Fe(III) ion. In a buffered medium, the Fe(II) ions reacted with 1,10-plenanthroline to form a red complex that was determined photometrically. The test iron oxide nanoparticles or biocompatible magnetic materials were first degraded to iron ions by adding sulfur acid and the pH of the resulting solution was adjusted to 2 to 8 by using 0.8 M $NaHCO_3$. It was observed that the Fe(II) ions were not converted to Fe(III) ions during the process. Without addition of ascorbic acid, the content of only Fe(II) ions was measured. The total iron ions were further measured by adding ascorbic acid to convert all iron ions to Fe(II) irons. The content of Fe(II) ions was determined to be about 4-15% relative to the total iron ions. Detailed results are shown in Table 1 below. Note that this table also includes the Fe(II) content of 1.26% for Feraheme, a commercial agent.

TABLE 1

| Measurement of Fe (II) contents | |
|---|---|
| Test sample | Fe (II) % |
| IO-OA (batch 1) | 4.32 |
| IO-OA (batch 2) | 5.78 |
| IO-OA (batch 3) | 4.19 |
| IO-OA (batch 4) | 10.88 |
| IO-OA (batch 5) | 6.84 |

TABLE 1-continued

| Measurement of Fe (II) contents | |
|---|---|
| Test sample | Fe (II) % |
| IO-OA (batch 6) | 8.55 |
| IO-OA (batch 7) | 6.53 |
| IO-OA (batch 8) | 9.64 |
| IO-OA/mPEG-silane-2000 (batch 1) | 5.90 |
| IO-OA/mPEG-silane-2000 (batch 2) | 6.29 |
| IO-OA/mPEG-silane-2000 (batch 3) | 7.35 |
| IO-OA/mPEG-silane-2000 (batch 4) | 8.44 |
| IO-OA/mPEG-silane-2000 (batch 5) | 6.87 |
| Feraheme | 1.26 |

These results indicate that biocompatible magnetic materials of this invention unexpectedly exhibited a much higher Fe(II) content as compared to Feraheme.

X-Ray Powder Diffraction (XRPD)

The structures of certain iron oxide nanoparticles and biocompatible magnetic materials were investigated by XRPD as follows.

Figure 2:
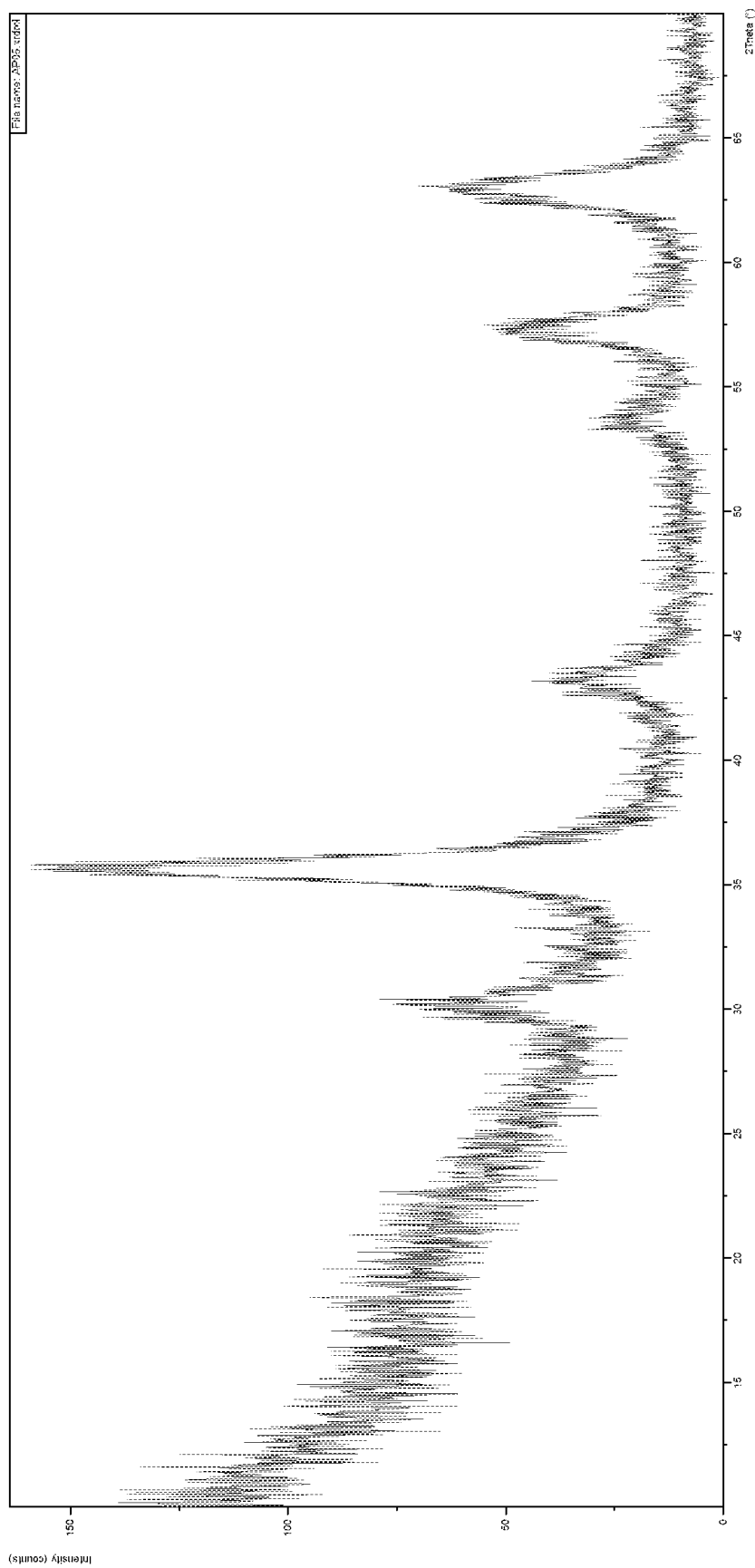
FIG. 2 is an XRPD pattern for IO-OA/methoxypolyethylene glycol-silane-2000 batch 2.

The test samples were dried to provide powder forms for XRPD measurements. FIGS. 1 and 2 show the XRPD patterns for IO-OA (batch 4) and IO-OA/mPEG-silane-2000 (batch 2), respectively.

As the differences between $\gamma$-$Fe_2O_3$ and $Fe_3O_4$ in XRPD are not discernable, these figures show that the crystalline structures of IO-OA (batch 4) and IO-OA/mPEG-silane-2000 (batch 2) could be $Fe_3O_4$, $\gamma$-$Fe_2O_3$, or the mixture of $Fe_3O_4$ and $\gamma$-$Fe_2O_3$.

Example 3: Relaxivity Measurement

A study was performed to measure the relaxivity of a biocompatible magnetic material prepared in EXAMPLE 1, as well as that for Feraheme, as follows.

Iron oxide solutions were prepared at various concentrations (0.1, 0.2, 0.3, 0.4, and 0.5 mM). T2 relaxation time of each solution was measured by Minispec mq 20 from the Bruker Corporation. A linear relationship was established between the reciprocal of the relaxation time as the ordinate axis and the concentration of the solution as the abscissa axis. The slope of the linear relationship was determined as the r2 relaxivity. Results are shown in Table 2 below.

TABLE 2

| Measurement of r2 relaxivity | |
|---|---|
| Test sample | r2 relaxivity $(mM \cdot s)^{-1}$ |
| IO-OA/mPEG-silane-2000 (batch 2) | 173 |
| Feraheme | 69 |

Unexpectedly, as shown in Table 2 above, IO-OA/mPEG-silane-2000 (batch 2), which contains 6.29% Fe(II) ions relative to the total irons, exhibited a r2 relaxivity value of 173 $(mM \cdot s)^{-1}$. By sharp contrast, Feraheme, which contains 1.26% Fe(II) ions relative to the total irons, exhibited a r2 relaxivity value of 69 $(mM \cdot s)^{-1}$.

These results indicate that biocompatible magnetic materials of this invention unexpectedly exhibited much higher r2 relaxivity as compared to Feraheme.

Example 4: Coupling with a Specific Targeting Agent

Described below are protocols for coupling a biocompatible magnetic material of this invention with a specific targeting agent.

Coupling with Folate

226 µL of folate solution (folate/dimethyl sulfoxide: 10 mg/mL) was placed in a 50 mL brownish round bottom flask. 5 mL of dimethyl sulfoxide (DMSO) and 176.5 µL of dicyclohexyl carbodiimide solution (dicyclohexyl carbodiimide/DMSO: 5 mg/mL) was added to the solution and stirred for one hour. Thereafter, 98.5 µl of NHS solution (N-hydroxysuccinimide/DMSO: 5 mg/mL) was added and stirred for additional one hour, 289 µL of ethylenediamine was then added to give a solution A.

1 mL of IO-OA/COOH-PEG-silane-2000 (4.48 mg Le/mL) and 10 ml of DMSO were placed in a 50 mL round bottom flask under vacuum. 176.5 µl of dicyclohexyl carbodiimide solution (dicyclohexyl carbodiimide/DMSO: 5 mg/mL) was added to the solution and stirred for one hour. Thereafter, 98.5 µl of NHS solution (N-hydroxysuccinimide/DMSO: 5 mg/mL) was added and stirred for additional one hour to give a solution B.

289 µL of solution A was added to solution B and the resulting solution was stirred for 8 hours. The resulting solution was added to a dialysis membrane (Mw: 3000) and distilled water was used for dialysis. The resulting solution was then concentrated to 2 mL by an ultra-filtration device to obtain a biocompatible magnetic material coupled with a targeting agent, i.e., folate-conjugated IO-OA/COOH-PEG-silane-2000.

Coupling with an Antibody

IO-OA/COOH-PEG-silane-2000 (4.48 mg Le/mL) was mixed with 5 mL of cold deionized water and kept on ice-bath. 1-Ethyl-3-(3-dimethylaminopropyl)carbodiimide ($10^{-6}$ mole) was added to the solution and stirred for 30 minutes. N-hydroxysuccinimide ($10^{-6}$ mole) was then added to the mixture and stirred for another 30 minutes. Antibody My10 (1 mL, 2 µg/mL) was added to the resulting mixture and reacted for 2 hours. The solution thus obtained was purified by passing through a magnetic sorting device to obtain a biocompatible magnetic material coupled with an antibody, i.e., My10-conjugated IO-OA/COOH-PEG-silane-2000.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims. It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A biocompatible magnetic material comprising:
   an iron oxide oleic acid nanoparticle; and
   one or more biocompatible polymers, each having formula (I) below, covalently bonded to the iron oxide oleic acid nanoparticle:

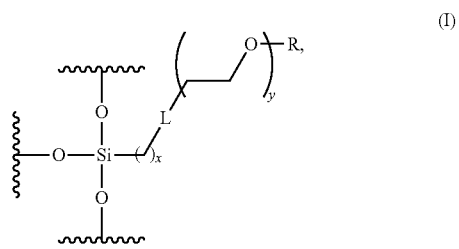

in which

R is H, $C_1$-$C_6$ alkyl, $C_2$-$C_6$ alkenyl, $C_2$-$C_6$ alkynyl, $C_3$-$C_{10}$ cycloalkyl, $C_1$-$C_{10}$ heterocycloalkyl, aryl, heteroaryl, a $C_1$-$C_{10}$ carbonyl group, or a $C_1$-$C_{10}$ amine group;

L is a linker;

x is 1 to 10; and y is 5 to 1000, wherein the iron oxide oleic acid nanoparticle contains 4-10% Fe(II) ions relative to the total iron ions.

2. The biocompatible magnetic material of claim 1, wherein the iron oxide oleic acid nanoparticle contains 4-8% Fe(II) ions relative to the total iron ions.

3. The biocompatible magnetic material of claim 1, wherein the linker is O, S, Si, $C_1$-$C_6$ alkylene, a carbonyl moiety containing two carbonyl groups and 2-20 carbon atoms, or a group having one of the following formulas:

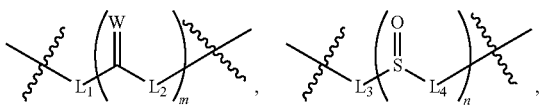

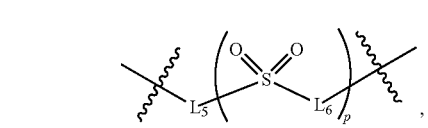

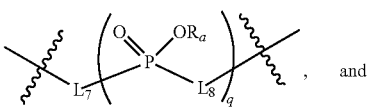

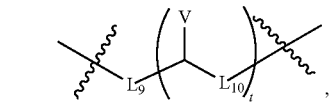

in which each of m, n, p, q, and t, independently, is 1-6; W is O, S, or $NR_b$; each of $L_1$, $L_3$, $L_5$, $L_7$, and $L_9$, independently, is a bond, O, S, or $NR_c$; each of $L_2$, $L_4$, $L_6$, $L_8$, and $L_{10}$, independently, is a bond, O, S, or $NR_d$; and V is $OR_e$, $SR_f$, or $NR_gR_h$, each of $R_a$, $R_b$, $R_c$, $R_d$, $R_e$, $R_f$, $R_g$, and $R_h$, independently, being H, OH, a $C_1$-$C_{10}$ alkyl, a $C_1$-$C_{10}$ heteroalkyl, a $C_3$-$C_{10}$ cycloalkyl, a $C_1$-$C_{10}$ heterocycloalkyl, aryl, or heteroaryl.

4. The biocompatible magnetic material of claim 1, wherein the iron oxide oleic acid nanoparticle is covalently bonded to one or more biocompatible polymers each having the following formula:

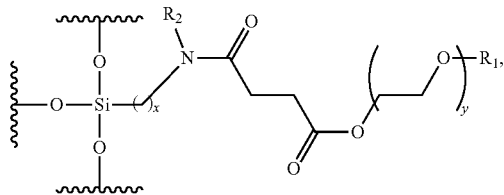

in which

R$_1$ is H, C$_1$-C$_6$ alkyl, C$_2$-C$_6$ alkenyl, C$_2$-C$_6$ alkynyl, C$_3$-C$_{10}$ cycloalkyl, C$_1$-C$_{10}$ heterocycloalkyl, aryl, heteroaryl, a C$_1$-C$_{10}$ carbonyl group, or a C$_1$-C$_{10}$ amine group;

R$_2$ is H, C$_1$-C$_6$ alkyl, C$_2$-C$_6$ alkenyl, C$_2$-C$_6$ alkynyl, C$_3$-C$_{10}$ cycloalkyl, C$_1$-C$_{10}$ heterocycloalkyl, aryl, or heteroaryl;

x is 1 to 10; and y is 5 to 1000.

5. The biocompatible magnetic material of claim 4, wherein R$_1$ is C$_1$-C$_6$ alkyl, a C$_1$-C$_{10}$ carbonyl group, or a C$_1$-C$_{10}$ amine group, and R$_2$ is H or C$_1$-C$_6$ alkyl.

6. The biocompatible magnetic material of claim 5, wherein R$_1$ is methyl, carboxyl, or amino, and R$_2$ is H.

7. The biocompatible magnetic material of claim 5, wherein R$_1$ is coupled to a specific targeting agent selected from the group consisting of an antibody, a protein, a peptide, an enzyme, a carbohydrate, a glycoprotein, a nucleotide, and a lipid.

8. The biocompatible magnetic material of claim 7, wherein the specific targeting agent is an antibody.

9. The biocompatible magnetic material of claim 1, wherein the iron oxide oleic acid nanoparticle is covalently bonded to one or more biocompatible polymers each having the following formula:

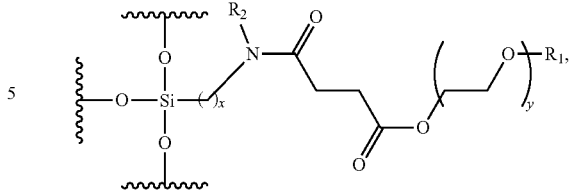

in which R$_1$ is methyl or carboxyl, R$_2$ is H, x is 1 to 10, and y is 5 to 1000.

10. A method of preparing a biocompatible magnetic material of claim 1, the method comprising:

providing a first solution that contains an iron oxide oleic acid nanoparticle in a first organic solvent, the iron oxide oleic acid nanoparticle containing 4-10% Fe(II) ions relative to the total iron ions;

providing a second solution that contains a biocompatible polymer of formula (I) in a second organic solvent;

mixing the first solution and the second solution to afford a mixed solution; and adding water to the mixed solution and stirring the resulting solution for at least 20 hours to obtain a biocompatible magnetic material.

11. The method of claim 10, wherein the iron oxide oleic acid nanoparticle is formed by mixing a hydroxide solution with an iron solution that contains a Fe(II) salt under an inert gas atmosphere.

12. The method of claim 11, wherein the iron solution contains a Fe(II) salt and a Fe(III) salt, in which the mole ratio of Fe(III)/Fe(II) is 1.70 or higher.

13. The method of claim 12, wherein the iron oxide oleic acid nanoparticle is formed by adding oleic acid in an amount of 100 mL or less per mole iron.

14. The method of claim 10, wherein each of the first organic solvent and the second organic solvent, independently, is toluene, aliphatic hydrocarbon, tetrahydrofuran, ketone, alcohol, alkyl ester, or a combination thereof.

15. The method of claim 11, wherein the inert gas is nitrogen or argon.

16. The method of claim 10, wherein the iron oxide-oleic acid nanoparticle contains 4-8% Fe(II) ions relative to the total iron ions.

* * * * *